US011426485B2

(12) United States Patent
Sambasivam et al.

(10) Patent No.: US 11,426,485 B2
(45) Date of Patent: Aug. 30, 2022

(54) PRESSURE SENSITIVE ADHESIVES WITH AMPHIPHILIC COPOLYMER

(71) Applicant: ConvaTec Technologies Inc., Las Vegas, NV (US)

(72) Inventors: Mahesh Sambasivam, Bridgewater, NJ (US); Joseph C. Salamone, Bridgewater, NJ (US); Ann Beal Salamone, Bridgewater, NJ (US); Xiang Yu, Bridgewater, NJ (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 301 days.

(21) Appl. No.: 16/109,536

(22) Filed: Aug. 22, 2018

(65) Prior Publication Data
US 2018/0362690 A1 Dec. 20, 2018

Related U.S. Application Data

(63) Continuation of application No. 13/382,227, filed as application No. PCT/US2010/041180 on Jul. 7, 2010, now Pat. No. 10,294,317.

(60) Provisional application No. 61/223,534, filed on Jul. 7, 2009, provisional application No. 61/228,023, filed on Jul. 23, 2009.

(51) Int. Cl.
| | |
|---|---|
| A61L 24/04 | (2006.01) |
| C09D 183/04 | (2006.01) |
| C08F 230/08 | (2006.01) |
| C09J 183/04 | (2006.01) |
| C08F 2/18 | (2006.01) |
| C09J 183/10 | (2006.01) |
| C08G 77/442 | (2006.01) |
| C09J 11/06 | (2006.01) |
| C09J 11/08 | (2006.01) |
| C09J 7/38 | (2018.01) |
| C08L 83/00 | (2006.01) |
| C08G 77/00 | (2006.01) |
| C09J 7/30 | (2018.01) |
| C09J 183/00 | (2006.01) |
| C09J 143/04 | (2006.01) |
| C08G 77/20 | (2006.01) |
| C08F 220/06 | (2006.01) |
| C08F 220/56 | (2006.01) |
| C09J 183/14 | (2006.01) |
| A61F 13/00 | (2006.01) |

(52) U.S. Cl.
CPC .............. *A61L 24/046* (2013.01); *C08F 2/18* (2013.01); *C08F 230/08* (2013.01); *C08G 77/00* (2013.01); *C08G 77/442* (2013.01); *C08L 83/00* (2013.01); *C09J 7/30* (2018.01); *C09J 7/38* (2018.01); *C09J 11/06* (2013.01); *C09J 11/08* (2013.01); *C09J 143/04* (2013.01); *C09J 183/00* (2013.01); *C09J 183/04* (2013.01); *C09J 183/10* (2013.01); *A61F 2013/00702* (2013.01); *C08F 220/06* (2013.01); *C08F 220/56* (2013.01); *C08G 77/20* (2013.01); *C09J 183/14* (2013.01); *C09J 2483/00* (2013.01)

(58) Field of Classification Search
CPC ....... C08F 230/08; C09J 183/10; C09J 143/04
See application file for complete search history.

(56) References Cited

U.S. PATENT DOCUMENTS

| | | | |
|---|---|---|---|
| 5,886,119 A * | 3/1999 | Schaedeli | ............ C08F 230/08 526/266 |
| 8,449,513 B2 | 5/2013 | Abrams | |
| 8,580,891 B2 * | 11/2013 | Liu | ........................ C09J 133/08 525/100 |
| 8,979,811 B2 | 3/2015 | Keleny et al. | |
| 9,968,480 B2 | 5/2018 | Nyberg | |
| 10,278,857 B2 | 5/2019 | Hansen et al. | |
| 10,294,317 B2 * | 5/2019 | Sambasivam | .......... C08G 77/00 |
| D862,691 S | 10/2019 | Fenton | |
| 10,434,015 B2 | 10/2019 | Taylor et al. | |
| 10,434,309 B2 | 10/2019 | Forsell | |
| 10,449,081 B2 | 10/2019 | Lee | |
| 10,449,082 B2 | 10/2019 | Johnsen | |
| 10,463,527 B2 | 11/2019 | Gallant et al. | |
| 10,470,917 B2 | 11/2019 | Chang | |
| 10,470,918 B2 | 11/2019 | Bendix | |
| 10,471,173 B2 | 11/2019 | Misawa | |
| 10,478,328 B2 | 11/2019 | Guidry et al. | |
| 10,478,329 B2 | 11/2019 | Oberholtzer et al. | |
| 10,478,330 B2 | 11/2019 | Wiltshire et al. | |
| 10,500,084 B2 | 12/2019 | Hansen et al. | |
| 10,500,315 B2 | 12/2019 | Chang et al. | |
| 10,507,318 B2 | 12/2019 | Jin et al. | |
| 10,512,562 B2 | 12/2019 | Kavanagh et al. | |
| 10,524,953 B2 | 1/2020 | Hanuka et al. | |
| 10,531,978 B2 | 1/2020 | Haas et al. | |
| 10,537,461 B2 | 1/2020 | Hanuka et al. | |
| 10,537,462 B1 | 1/2020 | Hatchett et al. | |
| 10,583,029 B2 | 3/2020 | Chang | |
| 10,588,773 B2 | 3/2020 | Tsai et al. | |
| 10,610,402 B1 | 4/2020 | Idowu et al. | |
| 10,617,554 B2 | 4/2020 | Luce | |
| 10,617,555 B2 | 4/2020 | James et al. | |
| 10,646,370 B2 | 5/2020 | Keleny et al. | |

(Continued)

FOREIGN PATENT DOCUMENTS

| | | |
|---|---|---|
| GB | 2534012 A | 7/2016 |
| GB | 2544180 A | 5/2017 |

(Continued)

Primary Examiner — Marc S Zimmer
(74) Attorney, Agent, or Firm — Taft Stettinius & Hollister LLP; Ryan O. White; Derek B. Lavender

(57) ABSTRACT

A silicone pressure sensitive adhesive with amphiphilic copolymers for maintaining adhesion in a moist environment. The amphiphilic copolymers for silicone adhesives include at least one silicone moiety and at least one hydrophilic segment. Such adhesives are applicable to securing medical devices to human skin.

15 Claims, No Drawings

(56) References Cited

U.S. PATENT DOCUMENTS

| | | |
|---|---|---|
| 10,653,551 B2 | 5/2020 | Apolinario et al. |
| 10,660,784 B2 | 5/2020 | Nishtala et al. |
| 10,660,785 B2 | 5/2020 | Kaufman et al. |
| 10,660,786 B2 | 5/2020 | Obst et al. |
| 10,729,806 B2 | 8/2020 | Bingol et al. |
| 10,736,769 B2 | 8/2020 | Grove Sund et al. |
| 10,744,224 B2 | 8/2020 | Israelson et al. |
| 10,758,398 B2 | 9/2020 | Murthy Aravalli et al. |
| 10,779,986 B2 | 9/2020 | Cox |
| 10,799,385 B2 | 10/2020 | Hansen et al. |
| 10,813,786 B2 | 10/2020 | Lysgaard |
| 10,813,787 B2 | 10/2020 | Dinakara et al. |
| 2004/0267216 A1 | 12/2004 | Udayakumar et al. |
| 2006/0058576 A1 | 3/2006 | Davies et al. |
| 2007/0037068 A1* | 2/2007 | Choi .................... G03F 7/0752 430/5 |
| 2010/0174253 A1 | 7/2010 | Cline et al. |
| 2011/0218507 A1 | 9/2011 | Andersen et al. |
| 2012/0041400 A1 | 2/2012 | Christensen |
| 2012/0109086 A1 | 5/2012 | Tsai |
| 2012/0136324 A1 | 5/2012 | Hanuka et al. |
| 2012/0179124 A1 | 7/2012 | Nguyen-Demary et al. |
| 2013/0072886 A1 | 3/2013 | Schertiger et al. |
| 2013/0226063 A1 | 8/2013 | Taylor et al. |
| 2014/0207094 A1 | 7/2014 | Chang |
| 2014/0221950 A1 | 8/2014 | Chang et al. |
| 2014/0288517 A1 | 9/2014 | Tsai et al. |
| 2014/0316360 A1 | 10/2014 | Ekfeldt et al. |
| 2015/0133881 A1 | 5/2015 | Freiding |
| 2015/0209172 A1 | 7/2015 | Richmann et al. |
| 2016/0151198 A1 | 6/2016 | Frampton et al. |
| 2016/0193003 A1 | 7/2016 | Todd et al. |
| 2016/0206469 A1 | 7/2016 | Prezelin |
| 2017/0007440 A1 | 1/2017 | Moavenian |
| 2017/0065451 A1 | 3/2017 | Brandt et al. |
| 2017/0209295 A1 | 7/2017 | Smith et al. |
| 2017/0209296 A1 | 7/2017 | Cailleteau |
| 2018/0064572 A1 | 3/2018 | Wiltshire |
| 2018/0235801 A1 | 8/2018 | Oellgaard et al. |
| 2018/0236207 A1 | 8/2018 | Shankarsetty |
| 2018/0303655 A1 | 10/2018 | Glithero et al. |
| 2018/0311066 A1 | 11/2018 | Hansen et al. |
| 2018/0344506 A1 | 12/2018 | Larsen |
| 2018/0360644 A1 | 12/2018 | Alvarez Ponce |
| 2018/0369474 A1 | 12/2018 | Falleboe et al. |
| 2019/0015241 A1 | 1/2019 | Lin et al. |
| 2019/0029868 A1 | 1/2019 | Grum-Schwensen et al. |
| 2019/0110919 A1 | 4/2019 | Beckers et al. |
| 2019/0117824 A1 | 4/2019 | Hansen et al. |
| 2019/0247549 A1 | 8/2019 | Nielsen |
| 2019/0321213 A1 | 10/2019 | Morrison, Sr. |
| 2019/0328571 A1 | 10/2019 | Adachi |
| 2019/0328572 A1 | 10/2019 | Weinberg et al. |
| 2019/0358076 A1 | 11/2019 | Blatt |
| 2019/0365560 A1 | 12/2019 | Timms et al. |
| 2019/0374372 A1 | 12/2019 | Seres et al. |
| 2019/0380860 A1 | 12/2019 | Eggert et al. |
| 2019/0380861 A1 | 12/2019 | Nordquist et al. |
| 2019/0380882 A1 | 12/2019 | Taylor et al. |
| 2020/0000624 A1 | 1/2020 | Gibbons et al. |
| 2020/0015996 A1 | 1/2020 | Schertiger |
| 2020/0030134 A1 | 1/2020 | Hopper |
| 2020/0038226 A1 | 2/2020 | Botten et al. |
| 2020/0038227 A1 | 2/2020 | Makar, Jr. |
| 2020/0038228 A1 | 2/2020 | Aravalli et al. |
| 2020/0038229 A1 | 2/2020 | Aravalli |
| 2020/0046541 A1 | 2/2020 | Sund et al. |
| 2020/0046542 A1 | 2/2020 | Guidry et al. |
| 2020/0046543 A1 | 2/2020 | Scalise et al. |
| 2020/0054476 A1 | 2/2020 | Miller |
| 2020/0054478 A1 | 2/2020 | Forsell |
| 2020/0060863 A1 | 2/2020 | Sund et al. |
| 2020/0061282 A1 | 2/2020 | Hvid et al. |
| 2020/0069455 A1 | 3/2020 | Oberholtzer et al. |
| 2020/0078206 A1 | 3/2020 | Chiladakis |
| 2020/0100931 A1 | 4/2020 | Schoess et al. |
| 2020/0100946 A1 | 4/2020 | Wohlgemuth et al. |
| 2020/0138619 A1 | 5/2020 | Cisko, Jr. et al. |
| 2020/0146944 A1 | 5/2020 | Moulton et al. |
| 2020/0163792 A1 | 5/2020 | Schertiger |
| 2020/0164196 A1 | 5/2020 | Jin et al. |
| 2020/0188160 A1 | 6/2020 | Udayakumar |
| 2020/0197213 A1 | 6/2020 | Frampton-Vallance et al. |
| 2020/0214872 A1 | 7/2020 | Tretheway et al. |
| 2020/0214873 A1 | 7/2020 | Tretheway et al. |
| 2020/0214875 A1 | 7/2020 | Tretheway et al. |
| 2020/0229962 A1 | 7/2020 | Torstensen et al. |
| 2020/0246173 A1 | 8/2020 | Schertiger et al. |
| 2020/0261254 A1 | 8/2020 | Williams et al. |
| 2020/0276044 A1 | 9/2020 | Tretheway et al. |
| 2020/0276045 A1 | 9/2020 | Bendavit |
| 2020/0281758 A1 | 9/2020 | Tan |
| 2020/0281761 A1 | 9/2020 | Tretheway et al. |
| 2020/0289307 A1 | 9/2020 | Tretheway et al. |
| 2020/0289308 A1 | 9/2020 | Tretheway et al. |
| 2020/0297524 A1 | 9/2020 | Hunt et al. |
| 2020/0306073 A1 | 10/2020 | Olsen et al. |
| 2020/0306074 A1 | 10/2020 | Speiermann et al. |
| 2020/0330258 A1 | 10/2020 | Hansen et al. |
| 2020/0330259 A1 | 10/2020 | Sund et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0338230 A1 | 10/2020 | Israelson et al. |

FOREIGN PATENT DOCUMENTS

| | | |
|---|---|---|
| GB | 2548673 A | 9/2017 |
| GB | 2550936 A | 12/2017 |
| GB | 2570526 A | 7/2019 |
| WO | 2015110544 A1 | 7/2015 |
| WO | 2015138190 A1 | 9/2015 |
| WO | 2015148035 A1 | 10/2015 |
| WO | 2018188706 A1 | 10/2018 |
| WO | 2018188707 A1 | 10/2018 |
| WO | 2019058126 A1 | 3/2019 |
| WO | 2019058127 A1 | 3/2019 |
| WO | 2019091526 A1 | 5/2019 |
| WO | 2019091527 A1 | 5/2019 |
| WO | 2019091528 A1 | 5/2019 |
| WO | 2019091529 A1 | 5/2019 |
| WO | 2019091532 A1 | 5/2019 |
| WO | 2019099662 A1 | 5/2019 |
| WO | 2019120424 A1 | 6/2019 |
| WO | 2019120429 A1 | 6/2019 |
| WO | 2019120430 A1 | 6/2019 |
| WO | 2019120433 A1 | 6/2019 |
| WO | 2019120434 A1 | 6/2019 |
| WO | 2019120437 A1 | 6/2019 |
| WO | 2019120438 A1 | 6/2019 |
| WO | 2019120439 A1 | 6/2019 |
| WO | 2019120442 A1 | 6/2019 |
| WO | 2019120443 A1 | 6/2019 |
| WO | 2019120444 A1 | 6/2019 |
| WO | 2019120446 A1 | 6/2019 |
| WO | 2019120448 A1 | 6/2019 |
| WO | 2019120449 A1 | 6/2019 |
| WO | 2019120450 A1 | 6/2019 |
| WO | 2019120451 A1 | 6/2019 |
| WO | 2019120452 A1 | 6/2019 |
| WO | 2019120458 A1 | 6/2019 |
| WO | 20190120432 A1 | 6/2019 |
| WO | 2019197291 A1 | 10/2019 |
| WO | 2019197971 A1 | 10/2019 |
| WO | 2019198012 A1 | 10/2019 |
| WO | 2019221830 A1 | 11/2019 |
| WO | 2019229267 A2 | 12/2019 |
| WO | 2019229268 A1 | 12/2019 |
| WO | 2019242828 A1 | 12/2019 |
| WO | 2020008470 A1 | 1/2020 |
| WO | 2020010766 A1 | 1/2020 |

(56) References Cited

FOREIGN PATENT DOCUMENTS

| WO | 2020014305 A1 | 1/2020 |
| WO | 2020016471 A1 | 1/2020 |
| WO | 2020035121 A1 | 2/2020 |

* cited by examiner

PRESSURE SENSITIVE ADHESIVES WITH AMPHIPHILIC COPOLYMER

CROSS-REFERENCE

This application is a continuation application of U.S. application Ser. No. 13/382,227, filed on Jan. 4, 2012, which is a U.S. National Phase Application of PCT/US2010/041180, filed on Jul. 7, 2010, which claims priority to U.S. Provisional Application No. 61/223,534, filed on Jul. 7, 2009, and U.S. Provisional Application No. 61/228,023, filed Jul. 23, 2009 which are incorporated by reference herein their entirety.

BACKGROUND OF THE INVENTION

Silicone pressure sensitive adhesives are widely used in transdermal drug delivery, wound dressings, scar dressings, and other healthcare applications. These adhesives are typically a condensation product of silicate resin and polydimethylsiloxane (PDMS) fluid, or a reactive blend of vinyl- and hydride-containing PDMS and a silicate resin cured via hydrosilylation reaction (Dow Corning Literature, *Silicone Pressure Sensitive Adhesives* (2002)). These adhesives are biocompatible, gentle on the skin, and securely attach medical devices to the body when the environment is dry. However, under moist conditions such as during skin perspiration, the hydrophobic silicone adhesives lose their adhesion to skin, which can lead to the dressing detaching from the body prematurely.

There is a need to improve the adhesion of these adhesives to skin in the presence of moisture. Traditionally, adhesion of skin adhesives under moist environments has been accomplished by adding water absorbing fillers such as hydrocolloids to pressure sensitive adhesives. The hydrocolloid fillers absorb moisture and soften, providing wet tack, thereby improving the adhesion to skin longer. However, the disadvantages of this approach are the reduction in the dry peel strength and tack properties of the adhesive due to the presence of hard fillers. In addition, because of the affinity of the fillers for water, they dissolve and leach out of the adhesive, which can leave a slimy residue on the skin after the dressing removal.

In order to improve the adhesion of silicone adhesives under a moist environment and to overcome the drawbacks of previous approaches, the present approach is to add a suitable amphiphilic silicone copolymer to a silicone pressure sensitive adhesive. An ideal amphiphilic silicone copolymer suitable for such applications should possess high cohesive strength, high moisture vapor transmission rate (MVTR), high pressure sensitive adhesion to surfaces, maintain adhesion even under moist conditions, and should not leach out components or leave a residue.

Commercially available amphiphilic silicone copolymers are typically based on grafted poly(ethylene glycol). These copolymers are low molecular weight liquids, which are typically used as surfactants or defoamers. Addition of such low molecular weight copolymers can affect the adhesive performance because of surface migration under moist conditions and lead to a reduction in adhesion.

Several amphiphilic silicone copolymers have been reported in the literature. Recently, G. Edrodi and J. P. Kennedy published the synthesis of amphiphilic conetworks of poly(ethylene glycol) (PEG) and polydimethylsiloxane (PDMS) (G. Edrodi and J. P. Kennedy, *J. Polym. Sci. Part A: Polym. Chem.*, 43, 4954-4963 (2005)). The amphiphilic conetworks exhibited swelling in water and hexane indicating bi-continuous phases.

Yildiz, et al. synthesized block copolymer of poly(vinyl pyrrolidone)-poly(dimethyl siloxane)-poly(vinyl pyrrolidone) (J. C. Kim, M. Song, S. Park, E. Lee, M. Rang, and H. Ahn, *J. Appl. Polym. Sci.*, 85, 2244-2253 (2002)). They prepared a di-isocyanate terminated PDMS which was then end-capped with t-butyl peroxide. This was used as a macroinitiator for N-vinyl pyrrolidone polymerization. The resulting copolymers showed lower glass transition temperature (Tg) than the homopolymer poly(vinyl pyrrolidone).

Graiver, et al. used aldehyde-functional silicones as reactive sites for vinyl copolymerization in the presence of a copper redox system (D. Graiver, G. T. Decker, Y. Kim, F. J. Hamilton, and H. J. Harwood, *Silicon Chemistry*, 1, 107-120 (2002)). Several graft and block copolymers including polymethacrylic acid and polyacrylic acid were incorporated into the silicone polymer. These polar segments were formed by the thermal decomposition of the t-butyl ester substituted polyacrylate segments.

Yilgor, et al. synthesized triblock copolymers of poly-caprolactone-PDMS, and poly(2-ethyl-2-oxazoline)-PDMS (I. Yilgor, W. P. Steckle, E. Yilgor, R. G. Freelin, and J. S. Riffle, *J. Polym. Sci. Part A: Polym. Chem.*, 27, 3673-3690 (1989)). For the caprolactone, hydroxyl-terminated PDMS was used as a macroinitiator, and for the oxazoline copolymers, benzyl chloride-terminated PDMS was used. The resulting copolymers with a silicone content of about 30-50% were shown to reduce the surface tension of plastics, such as PET, PMMA, and polyurethane.

Yildiz, et al. synthesized poly(N-isopropylacrylamide) hydrogels using diacrylate-terminated PDMS as the cross-linker (Y. Yildiz, N. Uyanik, and C. Erbil, *J. Macromol. Sci., Part A: Pure and Applied Chemistry*, 43, 1091-1106 (2006)). The resulting hydrogels were found to have higher compression moduli compared to the conventional crosslinker, N,N'-methylene bis-acrylamide. This was attributed to the hydrophobic interactions between PDMS segments in the network.

DETAILED DESCRIPTION OF THE INVENTION

The present invention includes silicone pressure sensitive adhesive compositions having novel amphiphilic silicone copolymers. The silicone pressure sensitive adhesive compositions according to the present invention are suitable for adhering to biological surfaces. The pressure sensitive adhesive includes an amphiphilic copolymer that is a reaction product of at least one silicone monomer or oligomer and at least one hydrophilic or amphiphilic monomer or oligomer, such that the amphiphilic copolymer:

does not dissolve in aqueous medium, and
  has a molecular weight greater than 10,000 g/mol The silicone monomer is a methacryloylalkylsiloxysilane, vinylalkylsiloxysilane, vinylalkoxysilane, and combinations thereof.

The silicone oligomer is polydimethylsiloxane with reactive groups selected from hydride, vinyl, methacrylate, acrylate, epoxy, carbinol, mercapto, acetoxy, amino, isocyanato, halide, hydroxyl, and combinations thereof.

The hydrophilic or amphiphilic monomer or oligomer is selected from acrylamides, N-alkylacrylamides, N,N-dialkylacrylamides, N-alkylaminoalkylacrylamides, methacrylamides, acrylic acid and its esters and salts, methacrylic acid and its esters and salts, amino methacrylates, N-alkylamino acrylates, N-alkylamino methacrylates, maleic anhydride and its derivatives, alkenyl anhdyride and its derivatives, vinyl ethers, reactive polyethers, polyisocyanates, polyesters, polyamides, polypeptides, polysaccharides, polyurethanes, and combinations thereof.

A silicone pressure sensitive adhesive composition as described above is suitable for adhering medical devices to biological surfaces when it comprises 0.1-100% of an amphiphilic copolymer of at least one silicone monomer or oligomer and at least one hydrophilic or amphiphilic monomer or oligomer that does not leach out in the presence of moisture. Such an adhesive is applicable for adhering medical devices, such as ostomy appliances, wound dressings, securement devices for surgical devices, intravenous delivery devices, catheters and infusion devices to human skin.

The amphiphilic copolymer structure is a block, alternating, random, branched, grafted, or a combination.

According to the present invention, a silicone pressure sensitive adhesive is blended with a sufficient amount of amphiphilic silicone copolymer so as to yield an adhesive that stays adhered under moist conditions and will not leach the copolymer in moisture. The invention also includes the synthesis of an amphiphilic silicone copolymer that is a pressure sensitive adhesive by itself.

Amphiphilic Copolymers:

The amphiphilic copolymers are based on a polymerizable silicone monomer copolymerized with hydrophilic and/or amphiphilic monomers.

Synthesis of Amphiphilic Tris(trimethylsiloxysilyl propyl) Methacrylate (TRIS) Copolymers The typical procedure for the synthesis of the poly(TRIS)-based random copolymers, via free radical polymerization, is as follows, using poly(TRIS-co-N,N'-dimethylaminoethyl methacrylate)(DMAEMA) (3:1 wt) as an example: 4.5 g TRIS and 1.5 g of DMAEMA were added into a 25 mL pressure resistant reaction flask. Then 0.045 g VAZO™ 67 was transferred into the flask. To the flask was then added 14 g ethyl acetate to afford a 30 wt % solution. The mixture was gently shaken until a clear solution was obtained. It was then flushed with nitrogen for 2 minutes, sealed, and let sit in a 65° C. oil bath for 6 hours. Following this, the solvent was evaporated at room temperature for 36 hours to produce a more viscous solution, which was then cast onto polyethylene film and further dried for 2 days, and finally vacuum dried. The copolymer, a soft, tacky solid, was washed in deionized water and H$_2$O/methanol 50/50 v/v mixture.

Similarly, other TRIS copolymers were made with methacrylic acid (MAA), N-vinylcaprolactam (NVCL), N-isopropylacrylamide (NIPAM), N-hydroxyethylacrylamide (NHEA), and methacrylate-terminated PDMS.

Pressure Sensitive Adhesive Compositions with Amphiphilic Silicone Copolymers

Example 1

The typical procedure for the preparation of silicone gel adhesive containing amphiphilic copolymer is as follows. A 1:1 ratio of NUSIL® MED-6345 Part A and Part B were taken. Then poly(TRIS-co-NIPAM) (3:1 monomer wt ratio) solution in HMDS was added so that the adhesive gel would eventually contain 5 wt % of solid copolymer. The mixture was thoroughly stirred and then coated on a polyurethane film and allowed to dry for 1 hour for evaporation of solvent. Later the adhesive was cured at 60° C. in the oven for 3 hours. In the case of 100% amphiphilic copolymer, the copolymer was dissolved in HMDS, coated onto to a polyurethane film and then dried in the oven. A 1-inch by 1.5-inch strip of the adhesive was tested on human subject for adhesion under dry and wet environment. For dry adhesion, the tape was secured to the abdominal area for 8 hours prior to removal. For wet adhesion, the tape was attached to abdominal skin of the human subject and then tape removed after an aerobic activity for 40-60 minutes. The results of the adhesion studies under dry and wet conditions are shown in Table 1.

TABLE 1

| No. | Sample Description | *Dry Adhesion | **Wet Adhesion |
|---|---|---|---|
| 1 | Control: MED ™ 6345 50/50 Parts A/B cured at 60° C. for 3 hr (17-65) | Adhered well | Completely delaminated |
| 2 | MED ™ 6345 50/50 Parts A/B + 5 wt % Poly(TRIS-co-NIPAM) 5 mol % NIPAM Cured at 60° C.-3 hr (17-83) | Adhered well | Good adhesion; no residue |
| 3 | Control: MED ™ 6345 30/70 Parts A/B cured at 60° C. for 3 hr (17-65) | Poor adhesion- delaminated completely | Completely delaminated |
| 4 | MED ™ 6345 50/50 Parts A/B + 10 wt % Poly(TRIS-co-DMAEMA) 5 mol % DMAEMA Cured at 60° C.-3 hr (17-83) | Adhered well | Weak adhesion; no residue |
| 5 | Poly(TRIS-co-Methacrylic acid) w/5 mol % methacrylic acid | Adhered very well- cold flow at edges | Very good adhesion left a lot of residue |

*Adhesion to abdominal skin for 8 hrs prior to removal (1.5" adhesive strip)
**Adhesion to abdominal skin followed by 40-60 minutes of activity prior to removal while perspiring
MED ™ 6345 is a two-part tacky silicone gel from NUSIL ® Technology.
VAZO ™ 67 is a free radical initiator from DUPONT ®.

Adhesives, 2, 4 and 5 are sufficient to secure an ostomy appliance, wound dressing, infusion device or other securement device to human skin.

Other Inventive Examples

The dry adhesion was measured at room temperature with a finger. The range of 0-5 was used (5=excellent adhesion, 0=no adhesion) for qualifying adhesion. The wet adhesive strength was measured using a tongue depressor which had been soaked in water for 5 min (and dipped in water and taken out before each measurement). The polymer films were cast from 20 wt % solutions in ethyl acetate, dried for 5 h, and equilibrated at 35° C. in the incubator overnight in a moist environment, then taken out and immediately measured. (The wet adhesion for all other materials was measured this way unless otherwise mentioned.) The cohesive strength indicates the ability of the adhesive film to be removed from the substrate without leaving residue or breaking apart. Cohesive strength was measured on a scale of 1 to 5 (5=no residue with intact film, 1=low cohesive strength with extensive residue remaining on the host substrate)

TABLE 2

Properties of blends of MED-6345(50/50) with poly(TRIS/NVCL)

| Formulation | Weight Ratio | Wet Adhesion | Cohesive Strength |
|---|---|---|---|
| MED ™-6345 (50/50) | 100:0 | 3 | 1 |
| MED ™-6345 (50/50) + poly(TRIS/NVCL) (3.6/1) | 100:5 | 3.5 | 1 |

TABLE 3

Properties of TRIS/MAA polymers (unpurified)

| Polymer (unpurified) | Dry adhesion[a] | Wet adhesion | Cohesive strength |
|---|---|---|---|
| TRIS/MAA (97/3) | 1/2.5 | 0 | 3.5 |
| TRIS/MAA (97.5/2.5) | 2.5/3.5 | 0.5 | 3.5 |
| TRIS/MAA (98/2) | 3/4 | 0.5 | 3 |
| TRIS/MAA (98.5/1.5) | 3/4 | 1 | 2.5 |
| TRIS/MAA (99/1) | 4/>5 | 1.5 | 1.5 |

[a]adhesion after pressing for ~0.5 seconds/adhesion after pressing ~10 seconds

TABLE 4

Properties of TRIS/MAA polymers (unpurified, heated at 60° C. overnight)

| Polymer (unpurified) | Dry adhesion[a] | Wet adhesion | Cohesive strength |
|---|---|---|---|
| TRIS/MAA (97/3) | 0/0.5 | 0 | 5 |
| TRIS/MAA (97.5/2.5) | 0.5/1 | 0 | 4.5 |
| TRIS/MAA (98/2) | 1/2 | 0 | 4 |
| TRIS/MAA (98.5/1.5) | 1.5/2.5 | 0.5 | 4 |
| TRIS/MAA (99/1) | 3/3.5 | 1 | 3.5 |

[a]adhesion after pressing for ~0.5 seconds/adhesion after pressing for ~10 seconds

TABLE 5

Properties of TRIS/MAA polymers (purified, not heated)

| Polymer (purified) | Dry adhesion[a] | Wet adhesion | Cohesive strength |
|---|---|---|---|
| TRIS/MAA (97/3) | 0/0 | 0 | 5 (brittle) |
| TRIS/MAA (97.5/2.5) | 0/0 | 0 | 5 (brittle) |
| TRIS/MAA (98/2)-10 mol % MAA | 0/0 | 0 | 5 (almost brittle) |
| TRIS/MAA (98.5/1.5) | 0/0.5 | 0 | 5 |
| TRIS/MAA (99/1)-5 mol % MAA | 1/1.5 | 0 | 4.5 |
| TRIS/MAA (99.5/0.5) | 1.5/2 | 0 | 4 |
| TRIS/MAA (99.75/0.25) | 1.5/2.5 | 0.5 | 4 |
| TRIS/MAA (99.875/0.125) | 2/3 | 0.5 | 3.5 |
| TRIS/MAA (99.9375/0.0625) | 3/3.5 | 1 | 2.5 |
| TRIS (100%) | 3.5/5 | 1 | 1.5 |

[a]adhesion after pressing for ~0.5 seconds/adhesion after pressing for ~10 seconds

TABLE 6

Properties of purified TRIS/NIPAM copolymers

| Polymer (purified) | Dry adhesion[a] | Wet adhesion | Cohesive strength |
|---|---|---|---|
| TRIS/NIPAM (5/1) | 0/0 | 0 | 5 (brittle) |
| TRIS/NIPAM (6/1) | 0/0.5 | 0 | 5 (almost brittle) |
| TRIS/NIPAM (7/1) | 0.5/1.5 | 0 | 5 |
| TRIS/NIPAM (8/1) | 1/2 | 0 | 5 |
| TRIS/NIPAM (12/1) | 1/2.5 | 0 | 5 |
| TRIS/NIPAM (15/1) | 1.5/3 | 0 | 4.5 |

TABLE 7

Properties of NIPAM/PDMS-macromonomer copolymers

| Polymer | Dry adhesion[a] | Wet adhesion | Cohesive strength |
|---|---|---|---|
| NIPAM/PDMS-macromonomer (1/2.5) | 0/0.5 | 0 | 5 (slightly rubbery) |
| NIPAM/PDMS-macromonomer (1/3) | 0/0.5 | 0 | 4.5 (somewhat rubbery) |
| NIPAM/PDMS-macromonomer (1/5) | 3/4.5 | 1 | 1 (rubbery but weak) |
| NIPAM/PDMS-macromonomer (1/7) | N/A | N/A | 0 |
| NIPAM/PDMS-macromonomer (1/10) | N/A | N/A | 0 |

PDMS-macromonomer purchased from GELEST ®, Inc.

We believe that this is the first time that a unique amphiphilic silicone copolymer has been synthesized that is used in a pressure sensitive adhesive composition and is capable of securely adhering medical devices to the body.

Tables 1-7 indicate that the pressure sensitive adhesives with amphiphilic copolymers of the present invention adhere well under dry and wet conditions. Furthermore, adhesion of these compositions to skin shows an improvement over silicone adhesives without the copolymers.

We claim:
1. A process, comprising:
   preparing an amphiphilic copolymer that is a free radical polymerization reaction product of at least one silicone monomer or oligomer and at least one hydrophilic or amphiphilic monomer or oligomer, wherein preparing the amphiphilic copolymer comprises:
   (i) combining the at least one silicone monomer or oligomer and the at least one hydrophilic or amphiphilic monomer or oligomer;
   (ii) adding a radical initiator;
   (iii) adding a solvent;
   (iv) heating the resulting mixture;
   (v) removing the solvent; and
   (vi) drying the resulting amphiphilic copolymer; and
   preparing a silicone pressure sensitive adhesive composition comprising the amphiphilic copolymer; and
   applying the silicone pressure sensitive adhesive composition to a body contacting surface of a device selected from the group consisting of an ostomy device, a wound dressing, an infusion device, a securement device for attaching surgical devices to the body, a securement device for attaching catheters to the body, a securement device for attaching intra-venous delivery devices to the body, and a combination of two or more thereof;
   wherein the amphiphilic copolymer:
   a) does not dissolve in aqueous medium;
   b) has a weight-averaged molecular weight greater than 10,000 g/mol; and c) does not leach out of the silicone pressure sensitive adhesive composition in the presence of moisture.

2. The process of claim 1, wherein the at least one silicone monomer or oligomer comprises a silicone monomer, and wherein the silicone monomer is selected from the group consisting of methacryloylalkylsiloxysilane, vinylalkylsiloxysilane, vinylalkoxysilane, and combinations thereof.

3. The process of claim 1, wherein the at least one silicone monomer or oligomer comprises a silicone oligomer, and wherein the silicone oligomer is polydimethylsiloxane with reactive groups selected from vinyl, methacrylate, acrylate, epoxy, and combinations thereof.

4. The process of claim 1, wherein the hydrophilic or amphiphilic monomer or oligomer is selected from acrylamides, N-alkylacrylamides, N,N-dialkylacrylamides, N-alkylaminoalkylacrylamides, methacrylamides, acrylic acid and its esters and salts, methacrylic acid and its esters and salts, amino methacrylates, N-alkylamino acrylates, N-alkylamino methacrylates, maleic anhydride and its derivatives, alkenyl anhdyride and its derivatives, vinyl ethers, and combinations thereof.

5. The process of claim 1, wherein the radical initiator is a diazo radical initiator.

6. The process of claim 1, wherein the amphiphilic copolymer is a random amphiphilic copolymer.

7. A process, comprising:
preparing a silicone pressure sensitive adhesive composition comprising an amphiphilic copolymer;
wherein the amphiphilic copolymer is a free radical polymerization reaction product of at least one silicone monomer or oligomer and at least one hydrophilic or amphiphilic monomer or oligomer;
wherein the amphiphilic copolymer does not dissolve in aqueous medium; and
wherein the amphiphilic copolymer has a weight-averaged molecular weight greater than 10,000 g/mol; and
applying the silicone pressure sensitive adhesive composition to a body contacting surface of a device selected from the group consisting of an ostomy device, a wound dressing, an infusion device, a securement device for attaching surgical devices to the body, a securement device for attaching catheters to the body, a securement device for attaching intra-venous delivery devices to the body, and a combination of two or more thereof.

8. The process of claim 7 wherein the device to which the silicone pressure sensitive adhesive composition is applied on a body contacting surface is an ostomy device.

9. The process of claim 7 wherein the device to which the silicone pressure sensitive adhesive composition is applied on a body contacting surface is a wound dressing.

10. The process of claim 7 wherein the device to which the silicone pressure sensitive adhesive composition is applied on a body contacting surface is a securement device for attaching surgical devices to the body, a securement device for attaching catheters to the body, or a securement device for attaching intra-venous delivery devices to the body.

11. The process of claim 7 wherein the device to which the silicone pressure sensitive adhesive composition is applied on a body contacting surface is an infusion device.

12. The process of claim 7, wherein the at least one silicone monomer or oligomer comprises a silicone monomer, and wherein the silicone monomer is selected from the group consisting of methacryloylalkylsiloxysilane, vinylalkylsiloxysilane, vinylalkoxysilane, and combinations thereof.

13. The process of claim 7, wherein the at least one silicone monomer or oligomer comprises a silicone oligomer, and wherein the silicone oligomer is polydimethylsiloxane with reactive groups selected from vinyl, methacrylate, acrylate, epoxy, and combinations thereof.

14. The process of claim 7, wherein the hydrophilic or amphiphilic monomer or oligomer is selected from acrylamides, N-alkylacrylamides, N,N-dialkylacrylamides, N-alkylaminoalkylacrylamides, methacrylamides, acrylic acid and its esters and salts, methacrylic acid and its esters and salts, amino methacrylates, N-alkylamino acrylates, N-alkylamino methacrylates, maleic anhydride and its derivatives, alkenyl anhdyride and its derivatives, vinyl ethers, and combinations thereof.

15. The process of claim 7, wherein the amphiphilic copolymer is a random amphiphilic copolymer.

* * * * *